United States Patent [19]

Köstner et al.

[11] 4,204,324
[45] May 27, 1980

[54] GUM MASK

[76] Inventors: Karl Köstner, In der Römerstadt 89, 6000 Frankfurt, Fed. Rep. of Germany; Aldo Lufi, Kaspar - Wüststr. 26, CH 8052 Zürich, Switzerland

[21] Appl. No.: 839,204

[22] Filed: Oct. 4, 1977

[30] Foreign Application Priority Data

Oct. 4, 1976 [CH] Switzerland .................... 012511/76

[51] Int. Cl.² ............................................. A61C 13/00
[52] U.S. Cl. .................................... 433/299; 433/199
[58] Field of Search ................. 32/2, 1; 260/DIG. 36

[56] References Cited

U.S. PATENT DOCUMENTS

| | | | |
|---|---|---|---|
| 810,184 | 1/1906 | Broadbent | 32/2 |
| 1,495,486 | 5/1924 | Joannides | 32/2 |
| 1,750,810 | 3/1930 | Miller | 32/2 |
| 2,659,970 | 11/1953 | Ingersoll, Jr. | 32/2 |
| 3,785,054 | 1/1974 | Van Handel | 32/2 |
| 4,024,636 | 5/1977 | Colpitts et al. | 32/2 |

*Primary Examiner*—Louis G. Mancene
*Assistant Examiner*—John J. Wilson
*Attorney, Agent, or Firm*—Cooper, Dunham, Clark, Griffin & Moran

[57] ABSTRACT

A gum mask and a method of preparing the same, said mask made from inert elastomers and being intended to cover the necks of teeth exposed by gum atrophy and bone decay through paradentosis.

17 Claims, 4 Drawing Figures

GUM MASK

This invention relates to a gum mask and a method of preparing the same. The mask is made from inert elastomers, i.e. elastomers resistant to chemical and mechanical influences in the mouth. The gum mask is useful to cover up such symptoms of paradentosis as bone decay around the alveoli and gum atrophy.

Bone decay and accompanying gum atrophy to progressive exposure of the necks of teeth, especially of the front teeth. Eventually, the teeth loosen as their support diminishes.

The exposed necks of the front teeth appear abnormal and inaesthetic. At present, among other measures, attempts are made to hide this undesirable state by covering the exposed necks of the teeth and replacing the shrunken gums with so-called paradentosis plates or dentures comprising burnt porcelain or synthetic material.

Apart from the fact that these paradentosis plates are very expensive to prepare and can only be mounted on healthy, sturdy teeth, the procedure, for obvious reasons, is not suitable for young people who are still growing.

Experiments have also been conducted using synthetic materials such as hard polyvinylchlorides or acrylates as masks. The rigidity and hardness of these materials resulted, however, in lesions of the gums through pressure and friction. Moreover, breaking of the masks could not always be avoided.

It is an object of the present invention to create a gum mask which is easy and inexpensive to prepare, remains soft and of good elasticity in spite of its high Shore hardness, thus putting only a minimum of pressure and friction on the gums, influences the speech of the wearer as little as possible and does not need to be mounted on healthy teeth.

The present invention provides a gum mask characterized by an oval, elongated and slightly arched shape simulating the original form of the atrophied gums and stretching to the crowns of the teeth. The mask is made from an inert elastomeric material. The mask has a front side with a surface structure and color that simulates the natural gums and a reverse side adapted to be mounted on the teeth. One longitudinal edge of the mask has an indentation in a region adapted to contact the frenulum, and the opposite longitudinal edge has several indentations, the number of which corresponds to the number of tooth necks to be covered. On the reverse side of said mask along the opposite longitudinal edge, ridges of the same elastomeric material are provided between the individual indentations, and preferably also at the ends of the two outermost indentations. The ridges extend into and fill in the gaps caused by bone decay and gum atrophy, thus closely embracing the exposed necks and roots of the teeth.

The gum mask of the invention is illustrated by the drawings.

FIG. 1 shows a model of front teeth in an upper jaw wherein the long necks 2 exposed by the shrinking of gums 1 are clearly visible.

Figure 2:
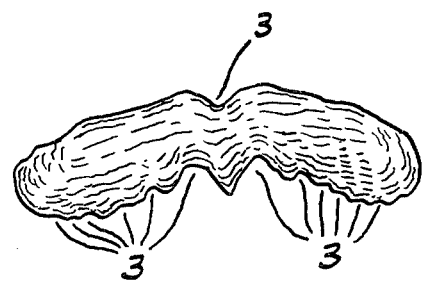
FIG. 2 is a front view of the gum mask according to the invention.

FIG. 2 shows the front side, i.e. the side adapted to contact the lips, of a gum mask prepared to fit the above model. The upper longitudinal edge is provided with an indentation 3 for the frenulum while the lower edge shows several indentations 3 simulating the shape of normal gums and covering the necks of the teeth. Suitable coloring and surface structure of the mask are chosen to resemble the natural appearance of gums.

Figure 1:
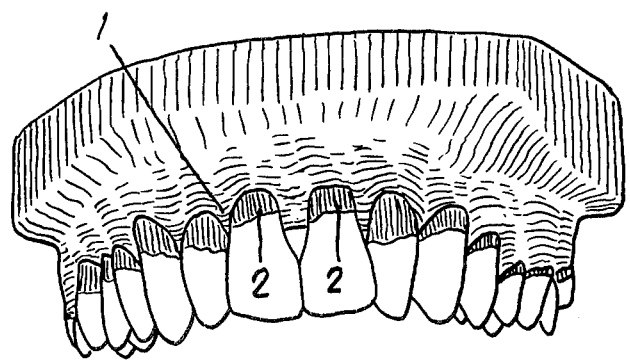
FIG. 1 is a model of front teeth in an upper jaw.
Figure 3:
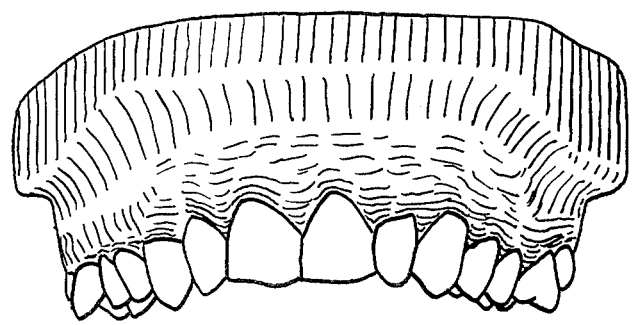
FIG. 3 is a model of the front teeth with the gum mask put into place.

FIG. 3 shows the same model as FIG. 1 but with the gum mask put into place.

Figure 4:
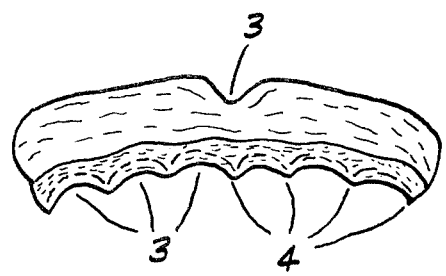
FIG. 4 is a view of the reverse side of the gum mask according to the invention.

Finally, in FIG. 4, the reverse side, i.e. the side turned away from the lips, of the gum mask having indentations 3 is shown. Clearly visible are the ridges 4 of the same material. These ridges extend into and fill in the gaps between the teeth, thus closely embracing the exposed necks and roots of the teeth and providing for a snug fit.

The gum mask of the present invention overcomes in a simple manner all disadvantages of former attempts to conceal exposed tooth necks and gum atrophy by using thermosetting elastomers, perferably polyurethane or silicone elastomers. Some of these elastomers, e.g., the silicone elastomers, are heat-curable as well as cold-setting. In spite of their high Shore hardness, these elastomers are soft, highly elastic, inert, i.e. resistant to chemical and mechanical influences in the mouth, and physiologically harmless. As they are transparent and almost invisible on the gums and may be colored in any way desired to match the respective gums, these elastomers provide perfect masks.

Another advantage of the gum mask of the invention is a marked improvement in the speech of the wearer. As the gaps caused by gum atrophy are filled in, hissing sounds, which have a strong psychological effect on the wearer, are prevented. Moreover, the mask provides support for loosened teeth.

The mask may be removed from the mouth and cleaned effectively at any time desired. The exposed necks of the teeth may thus be protected from caries.

An essential advantage of the mask according to the invention must also be seen in the fact that it is inexpensive to prepare and does not require manipulations on healthy teeth as in the case of so-called paradentosis plates.

The gum mask of the invention is safely held in place by the elasticity of the material and by the ridges on the reverse side which fill in the gaps caused by bone decay and gum atrophy and closely embrace exposed necks and roots of the teeth.

The permanently soft and pliable mask of the present invention may be prepared as follows:

An impression of the front teeth region of a patient is taken and a working model of plaster prepared from said impression. On the working model, missing portions of the gums are filled in with wax or a heat-stable material until the original state of the gums has been simulated. A mold for the gum mask is then prepared from the model thus obtained.

The elastomers used for preparing the gum mask, especially the heat-curable silicone rubbers, may be cured either by peroxidic cross-linking or by cross-linking under addition. Depending on the method of cross-linking employed, curing temperatures of between 100° C. and 180° C. are required. On account of these temperatures, the mold should be prepared from plaster or metals such as tin or metal alloys having a melting point above 200° C.

Silicone rubber worked into a dough-like consistency introduced into the mold and cured therein under pressure. The temperature and time needed for curing depend upon such factors as cross-linking agent used, type of mold and means of heating. For instance, in a plaster mold and under heating by means of a water bath, a method normally preferred in prosthetic dentistry, curing of the mask will take approx. 2 hours at 100° C. when 1 to 1.5% of bisbenzoylperoxide is used as a cross-linking agent. In metal molds needed for heat-curable silicone rubbers which are cross-linkable under addition, the mask will cure within 5 to 15 minutes at a temperature of 170° C. to 180° C., the curing time depending on the thickness of the material layer.

Heat-curable silicone rubbers containing 1 to 1.5% of bisbenzoylperoxide may also be cured in metal molds. In this case, curing will take 5 to 15 minutes at temperatures of between 110° C. to 130° C.

Two-component rubbers cross-linkable under addition, especially those setting at room temperature, are admixed in equal parts and may be cured in either metal or plaster molds.

As the gum mask suitably should have the color of the natural gums, the basic material is admixed with a sufficient amount of a physiologically acceptable dye.

We claim:

1. A gum mask for covering the necks of teeth exposed by gum atrophy, characterized by an oval, elongated and slightly arched shape adapted to the original form of the atrophied gums and stretching to the crowns of the teeth, said mask made from an inert elastomeric material having a front side having a surface structure and color that simulates the natural gums and a reverse side adapted to be mounted on said teeth, one longitudinal edge of said mask having an indentation (3) in a region adapted to contact the frenulum, the opposite longitudinal edge of said mask having several indentations (3), the number of which corresponds to the number of tooth necks to be covered, said reverse side of said mask which is adapted to contact the gums having ridges (4) along said opposite longitudinal edge between the indentations, said ridges being adapted to closely embrace the exposed necks (2) and roots of the teeth.

2. A gum mask according to claim 1 wherein the inert elastomeric material is a thermosetting elastomer.

3. A gum mask according to claim 2 wherein the thermosetting elastomer is a urethane elastomer.

4. A gum mask according to claim 3 having a Shore-A hardness of between 60° and 80° C.

5. A gum mask according to claim 2 wherein the thermosetting elastomer is a silicone elastomer.

6. A gum mask according to claim 5 having a Shore-A hardness of between 60° and 80° C.

7. A gum mask according to claim 2 wherein the thermosetting elastomer is a heat-curable or a cold-setting two-component silicone rubber cross-linkable under addition.

8. A gum mask according to claim 2 having a Shore-A hardness of between 60° and 80°.

9. A gum mask according to claim 1 wherein the inert elastomeric material is a heat-curable or cold-setting two-component silicone rubber cross-linkable under addition.

10. A gum mask according to claim 9 having a Shore-A hardness of between 60° and 80°.

11. A gum mask according to claim 1, having a Shore-A hardness of between 60° and 80°.

12. A gum mask according to claim 1 wherein the reverse side of said mask contacting the gums also has ridges along the opposite longitudinal edge at the ends of the two outermost indentations.

13. A gum mask according to claim 12 having a Shore-A hardness of between 60° and 80°.

14. A gum mask according to claim 12 wherein the inert elastomeric material is a thermosetting elastomer.

15. A gum mask according to claim 14 wherein the thermosetting elastomer is a heat-curable or a cold-setting two-component silicone rubber cross-linkable under addition.

16. A gum mask according to claim 15 having a Shore-A hardness of between 60° and 80°.

17. A gum mask according to claim 14 having a Shore-A hardness of between 60° and 80°.

* * * * *